United States Patent
Krishnan et al.

(10) Patent No.: US 6,961,621 B2
(45) Date of Patent: Nov. 1, 2005

(54) APPARATUS AND METHOD FOR STABILIZING AN IMPLANTABLE LEAD

(75) Inventors: Mohan Krishnan, Shoreview, MN (US); Avram Scheiner, Vadnais Heights, MN (US); Randy Westlund, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 639 days.

(21) Appl. No.: 10/004,708

(22) Filed: Dec. 4, 2001

(65) Prior Publication Data

US 2003/0105506 A1 Jun. 5, 2003

(51) Int. Cl.⁷ ................................................ A61N 1/05
(52) U.S. Cl. .............................................. 607/126
(58) Field of Search ............................... 607/119, 120, 607/126, 127, 128, 130, 131, 122, 123

(56) References Cited

U.S. PATENT DOCUMENTS

| | | | |
|---|---|---|---|
| 4,573,480 A | 3/1986 | Hirschberg | |
| 5,090,422 A | 2/1992 | Dahl et al. | |
| 5,304,218 A | * 4/1994 | Alferness | 607/122 |
| 5,358,516 A | 10/1994 | Myers et al. | |
| 5,387,233 A | 2/1995 | Alferness et al. | |
| 5,466,252 A | 11/1995 | Soukup et al. | |
| 5,554,178 A | 9/1996 | Dahl et al. | |
| 5,738,220 A | 4/1998 | Geszler | |
| 5,755,762 A | 5/1998 | Bush | |
| 5,782,898 A | 7/1998 | Dahl et al. | |
| 5,871,531 A | 2/1999 | Struble et al. | |
| 5,931,862 A | 8/1999 | Carson | |
| 6,021,354 A | 2/2000 | Warman et al. | |
| 6,055,457 A | 4/2000 | Bonner | |
| 6,304,786 B1 | 10/2001 | Heil, Jr. et al. | |
| 6,584,363 B2 * | 6/2003 | Heil et al. | 607/126 |
| 2002/0147486 A1 | 10/2002 | Soukup et al. | |

FOREIGN PATENT DOCUMENTS

| | | |
|---|---|---|
| EP | 0 606 688 A2 | 7/1994 |
| EP | 0 951 920 A2 | 10/1999 |
| WO | WO 00 56397 A | 9/2000 |

OTHER PUBLICATIONS

Nakao A, Miyazaki M, Oka Y, Matsuda H, Oishi M, Kokumai Y, Kunitomo K, Isozaki H, Tanaka N. Creation and use of a composite polyurethane expanded polytetrafluoroethylene graft for hemodialysis access. Acta Med Okayama. Apr. 2000;54(2):91–94. PMID: 10806530.

* cited by examiner

*Primary Examiner*—George Manuel
(74) *Attorney, Agent, or Firm*—Crawford Maunu PLLC

(57) ABSTRACT

A method and system for stabilizing an implantable lead system employs a lead having one or more sensing, pacing, or shocking electrodes. A sleeve arrangement of the lead includes one or more first locations comprising a first material that substantially prevents or inhibits tissue in-growth between the first locations and cardiac tissue contacting the first locations. The sleeve arrangement further includes one or more adhesion sites provided at one or more of the first locations. The adhesion sites promote tissue in-growth or attachment between the adhesion sites and cardiac tissue contacting the adhesion sites. The cardiac tissue may represent tissue of a cardiac structure of the heart or coronary vasculature of the heart.

59 Claims, 6 Drawing Sheets

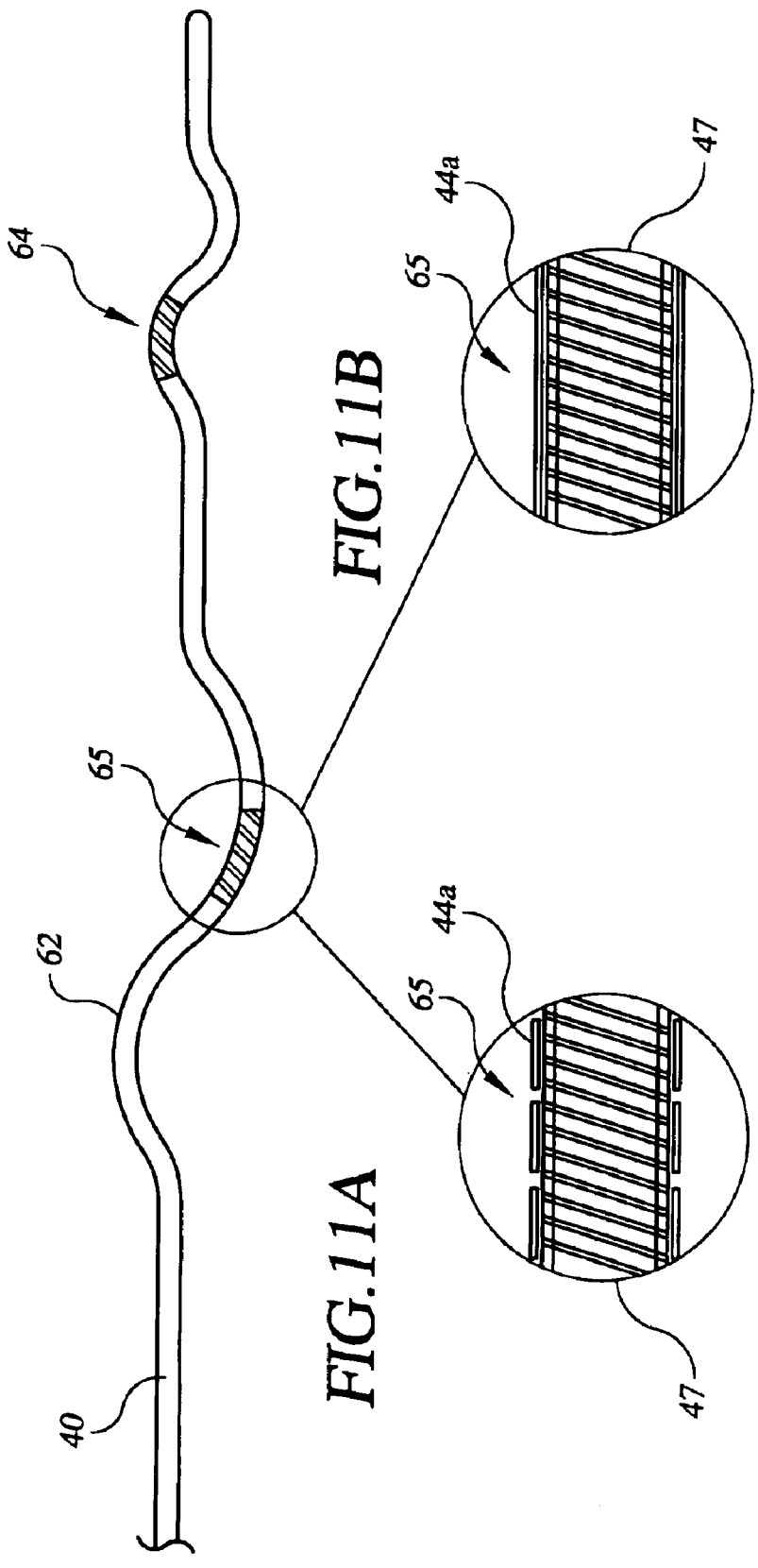

APPARATUS AND METHOD FOR STABILIZING AN IMPLANTABLE LEAD

FIELD OF THE INVENTION

The present invention relates generally to implantable leads and, more particularly, to systems and methods for stabilizing a lead in coronary sinus vasculature.

BACKGROUND OF THE INVENTION

Implantation of pacing and defibrillation leads in the coronary vessels is becoming increasingly common as atrial and heart failure therapies become more widely accepted. Implanting and stabilizing such leads in the coronary sinus, great vein, and the branch veins is critical to the efficacy of these and other therapies. It is often desirable or necessary to remove leads implanted in the coronary sinus vasculature for various reasons. Removal of these leads is problematic, especially if coil electrodes are employed on the lead.

Presently, there are no extraction tools available for the safe removal of coronary vein leads. Various tools have been developed for removing right ventricular leads and right atrial leads, for example, such as mechanical dissection sheaths, electrocautery sheaths, laser sheaths, and other powered sheaths. Such tools, however, are not suited for use within thin walled vessels. Presently available extraction tools, for example, can only be safely used to enter the proximal portions of the coronary sinus. The risk of significant damage to the vasculature is very high, which can result in cardiac tamponade and death. Consequently, physicians are presently limited to using locking stylets and simple traction as a means of removing coronary vein leads.

Various types of coatings applied to the electrodes have also been considered in order to facilitate easier removal of coronary vein leads. Although the extractability characteristics of leads can be improved using certain lead coatings, use of such coatings has been found to significantly reduce lead stability. For example, coated lead dislodgment rates of 25%–50% have been observed. As such, the gains in lead extractability realizable through use of conventional lead coatings are achieved at the cost of reduced lead stability.

There is a need in the industry for an improved coronary vein lead that exhibits improved extractability and stability characteristics. There exists a further need for such a lead that provides for controllable levels of extractability and stability. The present invention fulfills these and other needs, and provides a number of advantages over prior art approaches.

SUMMARY OF THE INVENTION

The present invention is directed to a system and method of stabilizing an implantable lead. The present invention provides particular advantages for leads designed to pass into or through the coronary sinus of a heart. According to one embodiment, the lead system includes a sleeve arrangement having one or more first locations comprising a first material that substantially prevents or inhibits tissue in-growth between the first locations and cardiac tissue contacting the first locations. The sleeve arrangement further includes one or more adhesion sites provided at one or more of the first locations. The adhesion sites promote tissue in-growth or attachment between the adhesion sites and cardiac tissue contacting the adhesion sites to enhance stabilization of the implantable lead. The cardiac tissue may represent tissue of a cardiac structure of the heart or coronary vasculature of the heart.

The adhesion sites, in one embodiment, define apertures in the sleeve at one or more first locations of the sleeve. For example, the adhesion sites may comprise exposed portions of one or more of the electrodes or other exposed portions of the lead's insulation or covering. According to another embodiment, the adhesion sites include a structure having a porous surface that promotes cardiac tissue in-growth or attachment at the adhesion sites. For example, a metallic annular structure may be disposed at the adhesion site. A metallic ring, for example, having porous surface characteristics may be employed to promote cellular adhesion at the adhesion site. The annular structure may incorporate an electrode, sensor or drug delivery arrangement. An annular electrode structure, for example, may incorporate a sensing, pacing or shocking electrode.

In accordance with a further embodiment, the adhesion sites comprise a material that promotes cardiac tissue in-growth or attachment at the adhesion sites. For example, the first material may comprise a first polymer material that substantially prevents tissue in-growth between the first locations and cardiac tissue contacting the first locations. The adhesion sites, in contrast, comprise a second polymer material that promotes tissue in-growth or attachment between the adhesion sites and cardiac tissue contacting the adhesion sites. The second polymer material may, for example, have a porosity, pore sizes or distribution of pore sizes that differ from that of the first polymer material. By way of further example, the second polymer material may differ in terms of hydrophobicity relative to the first polymer material.

In one embodiment, the first material comprises a first type of PTFE (polytetrafluoroethylene), and a second material of the adhesion sites comprises a second type of PTFE. In one particular arrangement, the first type of PTFE comprises a first type of ePTFE (expanded polytetrafluoroethylene), and the second type of PTFE comprises a second type of ePTFE. The second type of ePTFE preferably differs from the first type of ePTFE in terms of one or more of porosity, pore sizes or distribution of pore sizes.

The lead may further include a bias mechanism proximate one or more of the adhesion sites. The bias mechanism produces a force that biases an adhesion site against a cardiac or vessel structure. The bias mechanism may, for example, comprise a biased coil electrode, a biased insulation material disposed on an outer layer of the lead, a biased structure operatively coupled to a lumen disposed within the lead, or a biased structure disposed on the outer layer of the lead.

In accordance with another embodiment of the present invention, a lead system, such as a sensing, pacing or defibrillation lead system, includes a lead comprising at least one electrode. A sleeve or coating covers all or a portion of the electrode. A first fixation arrangement is provided with the lead. The first fixation arrangement provides fixation between a first portion of the lead and coronary sinus vasculature or cardiac structure of the heart. A second fixation arrangement is provided with the lead. The second fixation arrangement provides fixation between the coronary sinus vasculature or cardiac structure and a second portion of the lead.

In one configuration, the first fixation arrangement includes a first spiraled portion of the lead and the second fixation arrangement includes a second spiraled portion of the lead. According to another configuration, the first fixation arrangement includes a first spiraled portion of the lead, wherein the first spiraled portion includes at least a portion of the electrode. The second fixation arrangement, according to this configuration, includes a second spiraled portion of the lead distal to the first spiraled portion. The second spiraled portion may comprise silicone rubber or polyurethane rubber. According to another configuration, the first fixation arrangement or the second fixation arrangement may include one or more tines.

In accordance with another configuration of this embodiment, the first fixation arrangement includes a spiraled portion of the lead, and the second fixation arrangement comprises one or more adhesion sites provided with the sleeve for promoting coronary sinus tissue in-growth or attachment at the adhesion sites. The adhesion sites may comprise apertures in the sleeve, a material that promotes coronary sinus tissue in-growth or attachment at the adhesion sites, exposed portions of the electrode, a structure having a porous surface that promotes coronary sinus tissue in-growth or attachment at the adhesion sites, or a combination of these features.

According to another embodiment of the present invention, a lead system includes a lead having at least one electrode. A first fixation arrangement of the lead system includes a spiraled portion of the lead that provides a first fixation mechanism between the lead and coronary sinus tissue. The spiraled portion of the lead may comprise at least a portion of the electrode.

A second fixation arrangement of the lead provides a second fixation mechanism between the lead and coronary sinus tissue. The second fixation arrangement comprises a polymer sleeve arrangement encompassing the electrode. The polymer sleeve arrangement incorporates one or more adhesion sites for promoting coronary sinus tissue in-growth or attachment at the adhesion sites. One or more of the adhesion sites of the polymer sleeve arrangement, according to one configuration, comprises a first material that promotes coronary sinus tissue in-growth or attachment at the adhesion sites.

According to another configuration of this embodiment, the polymer sleeve arrangement, other than at the one or more adhesion sites, comprises a first material that prevents coronary sinus tissue in-growth. One or more of the adhesion sites comprises a second material that promotes coronary sinus tissue in-growth or attachment at the adhesion sites.

The second material, in one configuration, comprises a type of PTFE that promotes coronary sinus tissue in-growth or attachment. For example, the second material comprises a type of ePTFE that promotes coronary sinus tissue in-growth or attachment. In another configuration, the second material comprises a type of PET that promotes coronary sinus tissue in-growth or attachment. The first material may comprise a type of PTFE, ePTFE or PTE that prevents coronary sinus tissue in-growth.

One or more of the adhesion sites of the polymer sleeve arrangement may comprise one or more partial or complete gaps provided on the polymer sleeve arrangement. The gaps may comprise between about 1 percent and about 10 percent of a surface area of the polymer sleeve arrangement. The gaps may have a circumferential dimension and a longitudinal dimension, such that the circumferential dimension is greater than the longitudinal dimension. The gaps may alternatively have a circumferential dimension that is less than the longitudinal dimension. The gaps may also have a circumferential dimension that is substantially equal to the longitudinal dimension.

According to yet another embodiment of the present invention, a method of stabilizing a lead passing into a coronary sinus of a heart involves providing a sleeve arrangement on the lead. The sleeve arrangement includes one or more first locations comprising a first material and one or more adhesion sites provided at the one or more first locations. The method involves substantially preventing tissue in-growth between the first locations and cardiac tissue contacting the first locations. The method further involves promoting tissue in-growth or attachment between the adhesion sites and cardiac tissue contacting the adhesion sites to enhance stabilization of the lead passing into or through the coronary sinus. Electrical energy, such as pacing or defibrillating energy, may be produced at the adhesion sites. Electrical energy may also be sensed at the adhesion sites. Further, one or more physiologic parameters may be sensed at or proximate the adhesions sites.

Promoting tissue in-growth or attachment may involve promoting tissue in-growth or attachment via apertures defined at the adhesion sites. Promoting tissue in-growth or attachment, according to another approach, involves using a material that promotes cardiac tissue in-growth or attachment at the adhesion sites. In a further approach, promoting tissue in-growth or attachment involves using exposed portions of one or more of the electrodes or using a structure having a porous surface to promote cardiac tissue in-growth or attachment at the adhesion sites.

The method may involve the use of a first material comprising a first polymer material that substantially prevents tissue in-growth between the first locations and cardiac tissue contacting the first locations. The method may further involve promoting tissue in-growth or attachment by using a second polymer material at the adhesion sites that promotes tissue in-growth or attachment between the adhesion sites and cardiac tissue contacting the adhesion sites.

The method may also involve varying a porosity of the adhesion sites to be different from that of the first polymer material. Pore sizes and/or a distribution of pore sizes at the adhesion sites may be varied to be different from that of the first polymer material. According to a further approach, a bias force is generated at or proximate one or more of the adhesion sites.

In accordance with a further embodiment of the present invention, a method of stabilizing a lead passing into a coronary sinus of a heart involves providing a lead having at least one electrode. The method, according to this embodiment, involves stabilizing the lead at a first fixation location within a right atrium of the heart or a proximal portion of the coronary sinus. The method further involves stabilizing the lead at a second fixation location within a distal portion of the coronary sinus.

Stabilizing the lead at the first fixation location may involve mechanically stabilizing the lead at the first fixation location, and stabilizing the lead at the second fixation location may involve mechanically stabilizing the lead at the second fixation location. Mechanically stabilizing the lead may involve using a spiraled portion of the lead at one of the first or second fixation locations to stabilize the lead. Mechanically stabilizing the lead may also involve using a first spiraled portion of the lead at the first fixation location and using a second spiraled portion of the lead at the second fixation location to stabilize the lead.

According to another approach, the lead at the first fixation is mechanically stabilized, and stabilizing the lead at the second fixation location involves using cellular adhesion to coronary sinus vasculature to stabilize the lead at the second fixation location. According to a further approach, stabilizing the lead at the first fixation location involves using cellular adhesion to stabilize the lead at the first fixation location, and stabilizing the lead at the second fixation location involves mechanically stabilizing the lead at the second fixation location. A drug may further be delivered via the lead.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 10 illustrates a lead having a primary fixation arrangement and a secondary fixation arrangement to stabilize a lead implanted in the coronary sinus in accordance with an embodiment of the present invention;

FIGS. 11A and 11B illustrate two embodiments of an adhesion site provided proximate a spiraled portion of a lead in accordance with an embodiment of the present invention.

Figure 1:
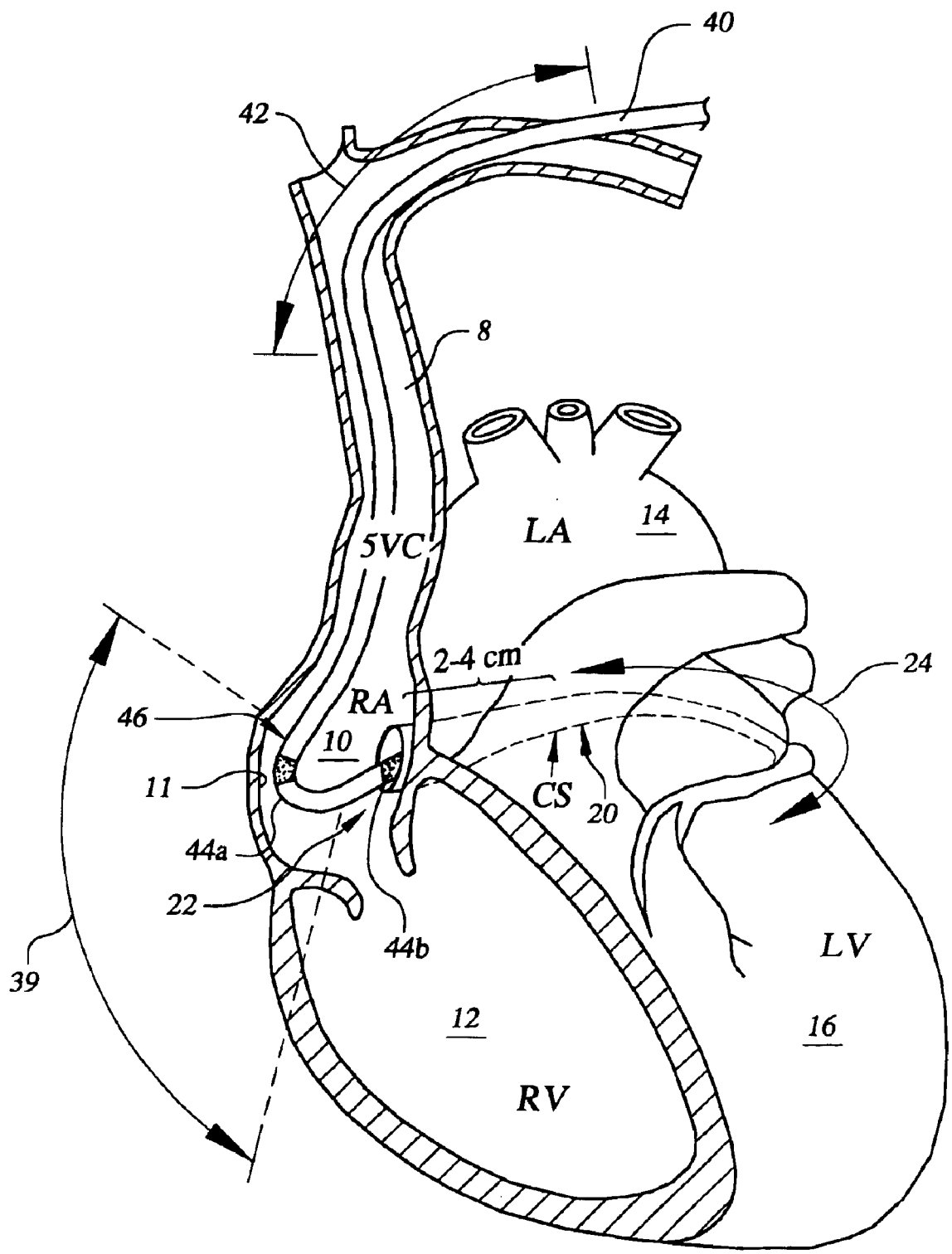
FIG. 1 is a partial cross-section of a human heart and a lead passing into a coronary sinus of the heart, the lead incorporating stabilizing features of the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, the present invention is directed to a lead apparatus that provides for increased stability after implant and improved extractability when removal of the lead apparatus is needed or desired. One particular advantage of a lead apparatus implemented according to the principles of the present invention concerns the ability to control the stability and extractability characteristics provided by the lead apparatus. Another advantage concerns the provision of a primary lead fixation mechanism and a secondary lead fixation mechanism for stabilizing a lead apparatus within coronary sinus vasculature, while providing for improved extractability characteristics.

A serious problem associated with conventional coronary sinus defibrillation leads, for example, involves extensive in-growth or attachment of tissue that occurs between and around surface variations and discontinuities, such as the electrode filars of the defibrillation leads. Such extensive tissue in-growth or attachment substantially increases the difficulty of extracting conventional coronary sinus defibrillation leads without damaging the coronary sinus vasculature.

According to one embodiment of the present invention, lead stability and extractability is improved by use of a polymer sleeve or coating provided on the lead and provision of an adhesion site or sites at strategic locations on the lead, including electrically active and/or electrically inactive locations of the lead. The polymer sleeve or coating provides for improved extractability of the lead, while the adhesion sites provide for increased stability at selected locations of the lead.

By way of example, a lead implemented in accordance with the present invention may include a standard defibrillation coil electrode provided with a polymer (e.g., silicone or polyurethane) insulating sleeve, a terminal end for connection to a pulse generator, and a distal end having one or more electrodes. A first material that prevents or inhibits tissue in-growth (e.g., fibrotic encapsulation or any other form of cellular adhesion), such as ePTFE, is strategically distributed along the lead at locations intended to physically contact selected locations in the coronary vasculature and/or selected locations on cardiac structures when properly implanted.

This first material is strategically interrupted with one or more regions designed for promotion of tissue in-growth or attachment, such regions collectively referred to herein as adhesion sites. These adhesion sites fibrose and attach more readily than the portions of the lead coated with the first material, and thus provide the necessary fixation to keep the lead in the desired implanted site. The adhesion sites may be locations within a cardiac structure, such as a wall of the right atrium, or locations within the coronary sinus vasculature. The term cardiac tissue as used herein is intended to represent any tissue of the heart, including vasculature of the heart.

The adhesion sites may take several forms, including materials, geometries, and surface modifications, for example, that serve to promote tissue in-growth or attachment. By way of example, suitable adhesion sites include short sections of exposed coil, metal rings with surface modifications resulting in porous surfaces (e.g., irox, powder coatings, etc.), and short sections of the polymer sleeve that have been modified to promote adhesion with cardiac tissue. Portions of the sleeve may be chemically or mechanically modified or altered by addition of appropriate materials to achieve a desired level of tissue in-growth or attachment promotion.

These adhesion sites thus define binding sites at which otherwise undesirable tissue in-growth or attachment between the lead and cardiac tissue is purposefully promoted. Moreover, the level or amount of tissue in-growth or attachment between the lead and cardiac tissue contacting the lead is controllable. As such, the integration of one or more adhesion sites provided at one or more strategic locations along the length of the lead advantageously provides for a high degree of control over the extractability and stability characteristics of a given lead and/or electrode.

In accordance with another embodiment of the present invention, stability of a lead provided heretofore by sole use of a primary fixation arrangement is improved by the use of a secondary fixation arrangement in addition to a primary fixation arrangement. According to one approach, a primary fixation arrangement includes a spiraled portion of the lead and the secondary fixation arrangement includes a second spiraled portion of the lead. The first spiraled portion typically encompasses all or part of a lead electrode.

Alternatively, the primary fixation arrangement may include a spiraled portion of the lead and the secondary fixation arrangement may include one or more adhesion sites of a type described previously and hereinbelow. By way of further example, the primary fixation arrangement may include a tine, exclusive of, or in addition to, a secondary fixation arrangement, such as a spiraled portion or one or more adhesion sites provided on the lead. The primary fixation arrangement plays an important short-term role in stabilizing the lead, while the slower developing cellular adhesion sites provide an important long-term role in enhancing stabilization of the lead. These and other advantageous features of a lead and/or electrode apparatus implemented in accordance with the principles of the present invention will be further discussed with reference to the figures.

Turning now to the figures and, more particularly, to FIG. 1, there is illustrated a partial cross-section of a human heart which is shown to include a superior vena cava (SVC) 8, a right atrium (RA) 10, a right ventricle (RV) 12, a left atrium (LA) 14, and a left ventricle (LV) 16. Also depicted in FIG. 1 is a coronary sinus (CS) 20 and the coronary sinus ostium 22, which is the opening of the coronary sinus 20 relative to the right atrium 10. A lead 40 is shown passing through the superior vena cava 8, right atrium 10, and coronary sinus ostium 22 in order to access the coronary sinus 20.

The lead 40 includes at least one, and typically several, electrodes. The electrodes provided on the lead 40 may be sensing, pacing, or defibrillation electrodes, or a combination of these electrode types. The lead 40 also includes locations at which cardiac tissue in-growth is prevented or inhibited, and further includes locations at which cardiac tissue in-growth or attachment is promoted. The locations of the lead 40 where cardiac tissue in-growth, attachment or encapsulation is purposefully promoted may define lead locations that are electrically active or electrically inactive. For example, a section of the lead 40 may include material, mechanical, or chemical surface features that entirely or partially encompass an electrode of the lead 40.

The illustrative embodiment depicted in FIG. 1 further shows a section 42 of an outer surface of the lead 40 designed to conform to a portion of the superior vena cava 8 that exhibits significant curvature or bending. This section 42 of the lead 40 preferably includes a coating or sleeve that prevents or inhibits cardiac tissue in-growth. A non-limiting, non-exhaustive list of coatings suitable for preventing or inhibiting cellular adhesion between the lead 40 and cardiac tissue contacting the lead 40 include PTFE, ePTFE, and PTE. These and other non-porous coating materials may be used at lead locations intended to be subjected to relatively high radius bending and/or other directional changes to conform to curvatures of particular cardiac structures and coronary vasculature. Such coatings also provide for reduced friction generated between the lead and contacting tissue and vasculature during implant and removal of the lead 40. The coating, sleeve or sheath employed to prevent or inhibit cardiac tissue in-growth in accordance with the present invention may be fabricated or formed using a variety of techniques, such as by spray coating, dip processing or deposition processing (e.g., plasma or chemical vapor deposition), for example.

FIG. 1 shows another section 39 of the lead 40 which is subject to a tight bend in the region of the right atrium 10 preceding the coronary sinus ostium 22. As in the case of section 42 of the lead 40 discussed above, this section 39 of the lead 40 preferably includes a coating or sleeve that prevents or inhibits cardiac tissue in-growth. In addition, this section 39 of the lead 40 is shown to include an adhesion site 44a integral to, or otherwise coupled to, the lead 40. In general, the location of an adhesion site 44a on the lead 40 is selected such that the adhesion site 44a promotes tissue in-growth or attachment relative to a venous or cardiac structure that is relatively easy and safe to access using various extraction tools.

The location of adhesion site 44a shown in FIG. 1 is selected such that adhesion site 44a contacts a wall surface 11 of the right atrium 10 when the lead 40 is properly implanted. The wall surface 11 represents a location where it is relatively easy and safe to use an extraction sheath, for example. The adhesion site 44a provides for controlled tissue in-growth or attachment between the wall surface 11 of the right atrium 10 and the adhesion site 44a.

To further enhance lead fixation provided between the wall surface 11 and adhesion site 44a, a bias mechanism 46 may be incorporated at or proximate the adhesion site 44a. The bias mechanism 46 produces a bias force that forces the adhesion site 44a against the wall surface 11 of the right atrium 10. The bias mechanism 46 may take many forms.

For example, a biased coil can be built into the lead 40 at or proximate the adhesion site 44a. A biased outer insulation layer may be provided on the lead 40 at or proximate the adhesion site 44a. A biased structure added to a lumen disposed within the lead 40 or added to an outside surface of the lead 40 lead at or proximate the adhesion site 44a may be employed to produce the desired bias force. It is understood that a bias mechanism 46 provided at or proximate the adhesion site 44a may also be employed at or near other adhesion sites located elsewhere on the lead 40 to force such adhesion sites against venous or cardiac structures.

The lead 40 is shown to include another adhesion site 44b strategically located on the lead 40 so that the adhesion site 44b is situated at the coronary sinus ostium 22 when the lead 40 is properly implanted. This or an additional adhesion site may be provided on the lead 40 to contact the proximal 2–5 cm of the coronary sinus 20, which can typically be accessed with extraction tools in a safe manner. Region 24 of the coronary sinus 20 represents portions of the coronary sinus 20 which are extremely difficult to access with extraction tools, and as such, represents locations where the use of adhesion sites should be limited or excluded.

Figure 2:
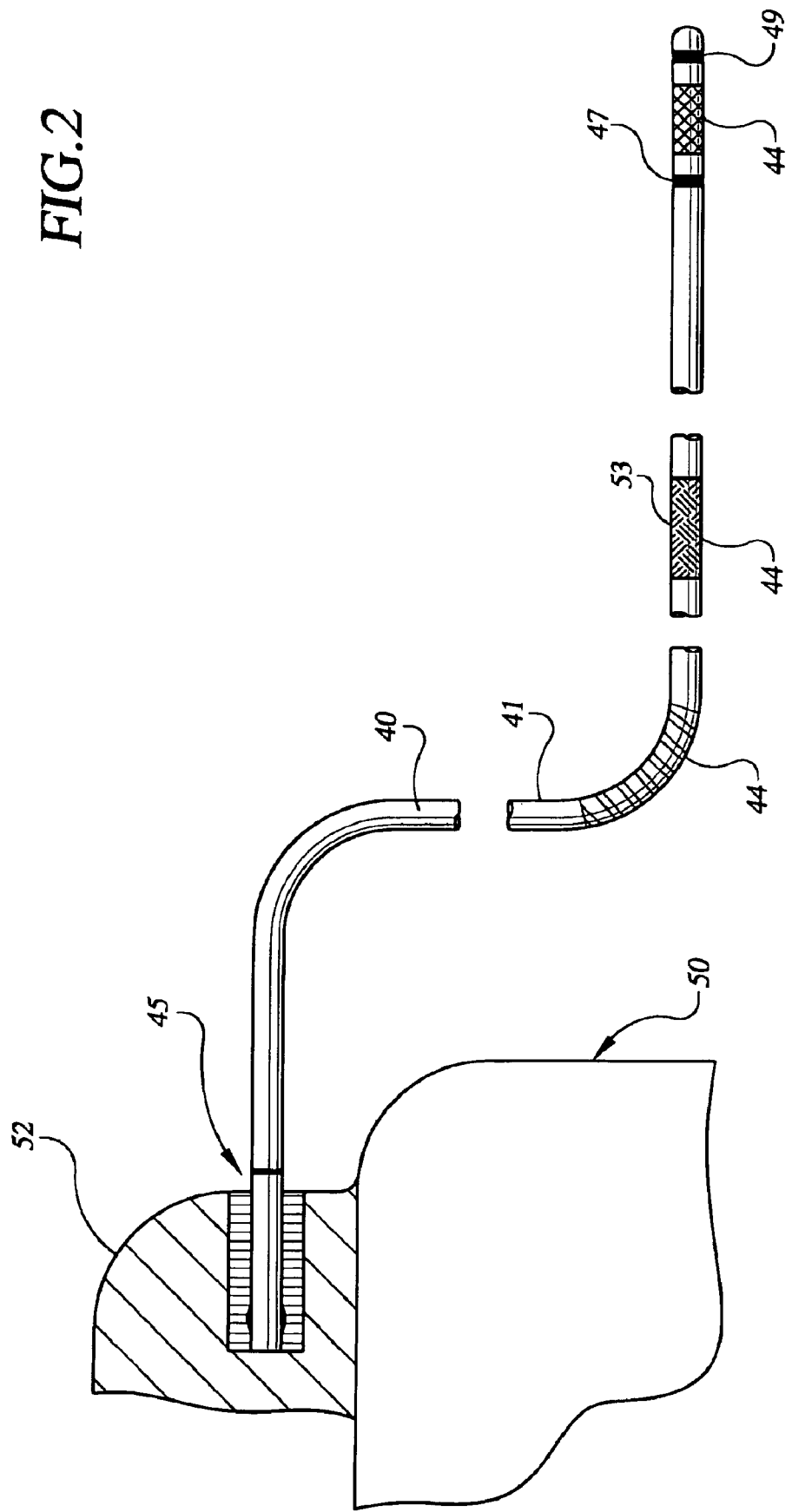
FIG. 2 is an exaggerated depiction of a lead system that includes several adhesion sites incorporated into the lead structure in accordance with an embodiment of the present invention.

FIG. 2 is an exaggerated depiction of a lead system that includes several adhesion sites 44 incorporated into the lead structure in accordance with an embodiment of the present invention. The lead system includes a lead 40 that incorporates one or more electrodes, including a coil electrode 53. The lead 40 may also incorporate tip and ring electrodes 49 and 47. The coil electrode 53 is typically supported by a silicone or polyurethane insulating sleeve to provide insulation between the various electrical components. The lead system further includes a terminal end 45 for establishing physical and electrical connection with a connector block 52 of an implantable medical device 50, such as a pacemaker, cardioverter, defibrillator, cardiac monitor, re-synchronizer or a device that incorporates the functions of two or more of these devices.

The outer surface 41 of the lead is preferably provided with a first coating or sleeve that prevents or inhibits cardiac tissue in-growth, such as ePTFE for example. As previously discussed, this first coating or sleeve is strategically distributed along the outer surface 41 of the lead 40 that, when implanted, will reside in the coronary vasculature and cardiac structures. This first coating or sleeve is strategically interrupted with one or more interspersed segments of a second coating, sleeve or mechanical feature that promotes tissue in-growth or attachment, such as at one or more adhesion sites 44 along the lead 40. It is noted that an adhesion site need not be disposed within a portion of the lead 40 that is provided with a coating or sleeve that prevents or inhibits cardiac tissue in-growth, but may instead be situated at or within an untreated section of the outer surface 41 of the sleeve.

The lead system may also be configured for drug delivery applications. The lead 40 may be used to pump or otherwise transport a drug from a proximal pumping location to a distal section of the lead 40, typically via an open lumen or other conduit of the lead 40. The electrode 49 and/or 47 may alternatively be representative of a drug delivery arrangement that dispenses a drug from the lead 40 to the cardiac structure, vessel or feature of interest. Commonly owned U.S. Pat. No. 6,298,272 discloses various suitable approaches to delivering a drug via a lead 40, which is hereby incorporated herein by reference.

The lead system may further be configured to include on or more sensors of various types, alone or in combination with one or more electrodes and/or a drug delivery mechanism. For example, the electrode 49 described above with reference to FIG. 2 may instead be representative of a physiologic sensor. The physiologic sensor 49 may include one or a combination of an accelerometer or other activity sensor, a pressure sensor, an oxygen sensor or a temperature sensor, for example.

Figure 3:
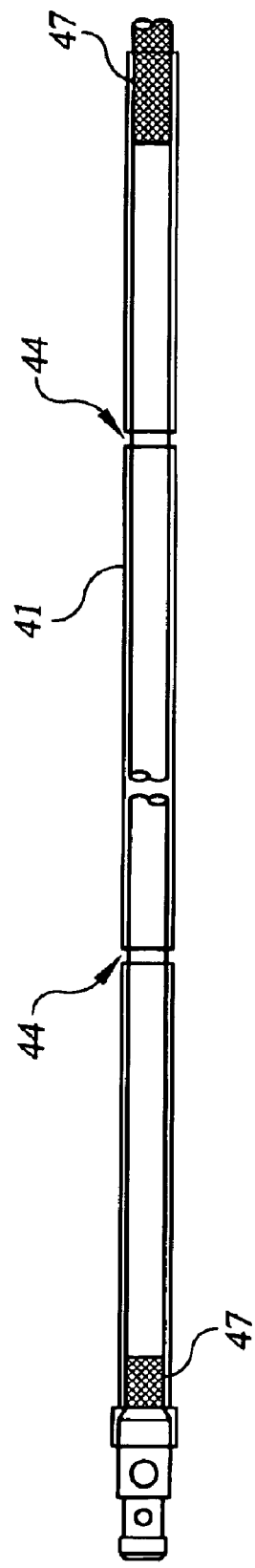
FIG. 3 is a depiction of a coronary sinus electrode configuration which incorporates one or more adhesion sites according to an embodiment of the present invention.

FIG. 3 is a depiction of a coronary sinus electrode configuration which incorporates one or more adhesion sites according to an embodiment of the present invention. According to this embodiment, the electrode structure 47 includes a covering 41 of ePTFE or other suitable material that prevents or inhibits tissue in-growth. The electrode covering 41 is provided with one or more adhesion sites 44 for promoting tissue in-growth or attachment thereat. The size, shape, material, and surface properties of the adhesion sites 44 are judiciously selected to provide the desired degree of lead/electrode fixation at the sites vis-à-vis the tissue in-growth and attachment adhesion mechanism exploited by the present invention. The adhesion sites 44 provided within a given electrode structure generally comprises about 1 percent to about 10 percent of the surface area of the electrode structure.

The adhesion sites of the present invention may be fabricated into or onto a lead, and may be comprised of materials, geometries, surface features, surface modifications, or mechanical features that promote tissue in-growth or attachment. Several types of suitable adhesion sites were described previously. FIGS. 4–9 depict in greater detail several embodiments of an adhesion site that may be provided at selected locations on a lead or electrode.

Figure 4:
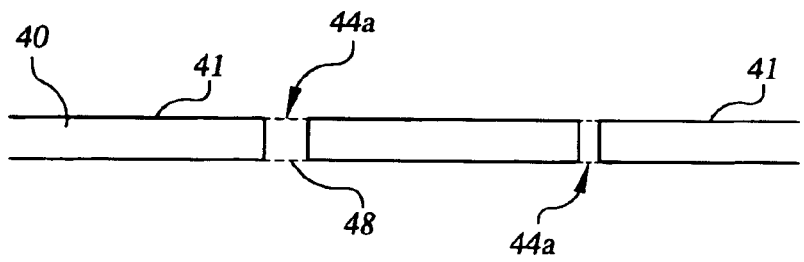
FIG. 4 illustrates an embodiment of an electrode or lead that incorporates one or more adhesion sites in the form of gaps provided in a polymer covering of the lead/electrode in accordance with an embodiment of the present invention.

FIG. 4 illustrates an embodiment of an electrode or lead portion 40 that incorporates one or more adhesion sites 44a in the form of gaps 48 provided in the polymer covering 41 of the lead/electrode 40. In one configuration, the polymer covering is fabricated from ePTFE disposed over an electrode. One or more continuous gaps 48 are provided in the ePTFE covering 41. It is understood that covering 41 may be fabricated from another material that inhibits tissue in-growth, such as PTFE, PTE or other suitable polymer or composite material. The gaps 48 expose underlying material of the electrode (or lead) that promotes tissue in-growth or attachment.

Figure 5:
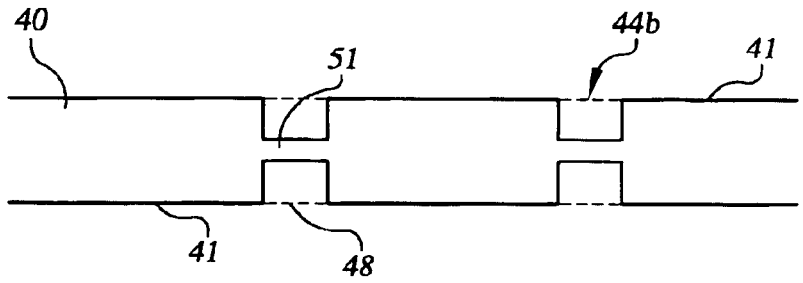
FIG. 5 illustrates an embodiment of an electrode or lead that incorporates one or more adhesion sites in the form of partial gaps provided in a polymer covering of the lead/electrode in accordance with an embodiment of the present invention.

FIG. 5 illustrates another embodiment of a lead or electrode covering 41 that incorporates one or more adhesion sites 44b. The embodiment of FIG. 5 is similar to that shown in FIG. 4, in that the adhesion sites 44b comprise gaps 48 in the covering 41. In contrast to the continuous gaps depicted in FIG. 4, the covering or sleeve 41 shown in FIG. 5 is fabricated to include bridge material 51 that spans across separated portions of the covering or sleeve 41. Inclusion of such bridge material 51 may enhance positional stability of the otherwise separated sleeve portions that define the adhesion site 44b.

Figure 6:
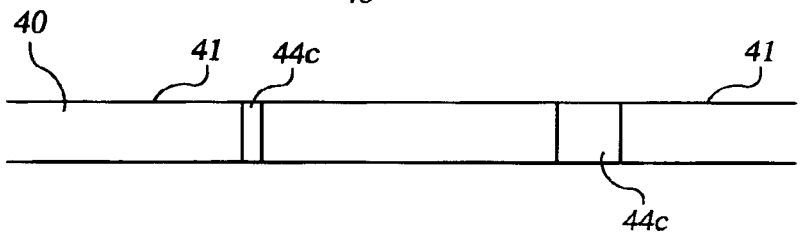
FIG. 6 illustrates a lead or electrode covering that incorporates one or more adhesion sites that represent portions of the covering having characteristics that differ from the bulk material of the lead/electrode covering in accordance with an embodiment of the present invention.

FIG. 6 illustrates a lead or electrode covering 41 that incorporates one or more adhesion sites 44c that represent portions of the covering having characteristics that differ from the bulk material of the lead/electrode covering 41. For example, the adhesion sites 44c shown in FIG. 6 may represent sections of the polymer covering 41 that have been modified to promote cellular adhesion, such as by incorporation of a chemical, material or mechanical feature that promotes mild fibrotic encapsulation. The adhesion sites 44c may represent chemically or mechanically treated portions of the covering 41. The adhesion sites 44c may also represent sections in which the bulk material of the covering 41 has been altered or replaced by a material that promotes cellular adhesion.

By way of example, the bulk material of the covering 41 that encompass an adhesion site 44c may be fabricated using ePTFE, PTFE or PET material that has properties (e.g., microstructure, porosity, pore size, distribution of pore sizes, affinity for water) that prevents or inhibits tissue in-growth. The adhesion sites 44c, however, may represent portions of the ePTFE, PTFE or PET material that have been altered to exhibit properties that promote tissue in-growth or attachment. For example, a lead or electrode covering 41 fabricated from ePTFE may include adhesion sites 44c defined by ePTFE material that has a microstructure, porosity, pore size, distribution of pore sizes, and/or affinity for water (e.g., hydrophilic property) that promotes tissue in-growth or attachment.

Figure 7:
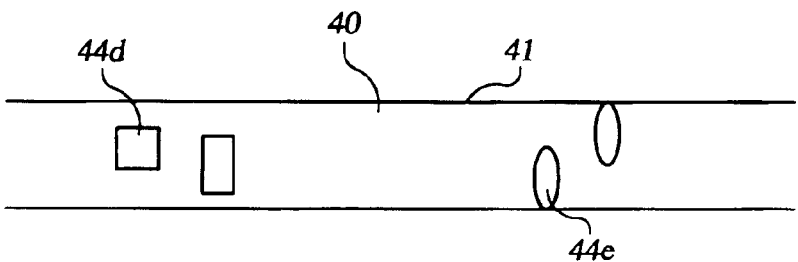
FIG. 7 illustrates adhesion sites provided on a lead having square or rectangular geometries in accordance with an embodiment of the present invention.
Figure 8:
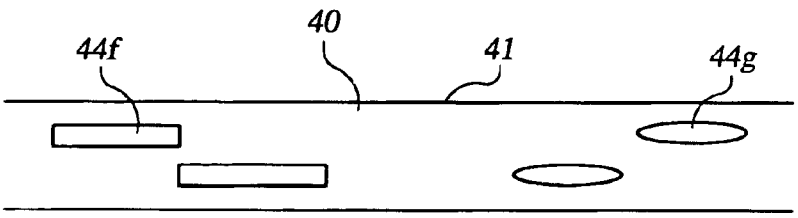
FIG. 8 illustrates adhesion sites provided on a lead having round or oval geometries in accordance with an embodiment of the present invention.

FIGS. 7 and 8 are intended to illustrate that adhesion sites 44 may be incorporated into a lead or electrode structure having a wide range of sizes, orientations, configurations, and material make-up. FIG. 7, for example, illustrates square or rectangular shaped adhesion sites 44d. Round or oval shaped adhesion sites 44e are also depicted in FIG. 7. The adhesions sites 44d, 44e shown in FIG. 7 generally have a circumferential dimension that is larger than a axial dimension, with the exception of a square shaped adhesion site. The adhesion sites 44d, 44e may represent apertures or voids that are punched in the lead/electrode covering 41. Alternatively, these adhesion sites 44d, 44e may represent regions of treated covering material that promote cellular adhesion.

FIG. 8 illustrates adhesion sites 44f, 44g having elongated rectangular and oval shapes, respectively. The adhesions sites 44f, 44g shown in FIG. 8 generally have an axial dimension that is larger than a circumferential dimension. As in FIG. 7, the adhesion sites 44f, 44g may represent apertures or voids that are punched in the lead/electrode covering 41 or regions of treated covering material that promote cellular adhesion.

Figure 9:
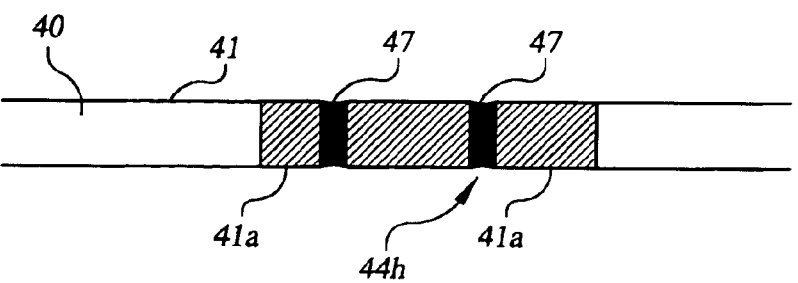
FIG. 9. Illustrates two additional embodiments of an electrode covering that incorporates one or more adhesion sites of the present invention.

FIG. 9 is another embodiment of an electrode covering 41 that incorporates one or more adhesion sites 44h. In this embodiment, a portion 41a of the covering 41 is coated or provided with a sleeve of a polymer that prevents cellular adhesion, such as ePTFE. Two gaps 44h are provided to expose portions of an electrode 47, such as a defibrillation coil electrode.

FIG. 9 may also be viewed to include adhesion sites according to a further embodiment. In this embodiment, a portion 41a of the covering 41 is coated or provided with a sleeve of a polymer that prevents cellular adhesion, such as ePTFE. One or more polymeric, metallic, or composite rings 44h having surface features that promote tissue in-growth or attachment are incorporated in or on the electrode structure of the lead.

Turning now to FIG. 10, there is illustrated another embodiment of the present invention in which a primary fixation arrangement and a secondary fixation arrangement are provided to stabilize a lead implanted in the coronary sinus. The lead 40 shown in FIG. 10 includes a primary spiraled portion 62 of the lead 40 that encompasses or is proximate an electrode 47. The primary spiraled portion 62 provides a primary fixation mechanism for stabilizing the position of the lead 40 within the coronary sinus. An exemplary illustration of a primary spiraled lead portion is disclosed in U.S. Pat. Nos. 5,387,233 and 5,871,531, which are hereby incorporated by reference in their respective entireties. One or more sections 65 of the primary spiraled portion 62 may include adhesion sites 44 of a type previously described. For example, an adhesion site 44a incorporated within the primary spiraled portion 62 may comprise one or more gaps, as is shown in FIG. 11A. An adhesion site 44c incorporated within the primary spiraled portion 62 may alternatively comprise one or more treated portions of the covering material that promote cellular adhesion, as is shown in FIG. 11B.

In addition to the primary spiraled portion 62, the lead 40 shown in FIG. 10 further incorporates a secondary spiraled portion 64. The secondary spiraled portion 64 is situated distal to the primary spiraled portion 62 on the lead 40. The secondary spiraled portion 64 may be of a construction similar or equivalent to that of the primary spiraled portion 62. The secondary spiraled portion 64 provides a secondary means of fixing or otherwise stabilizing the position of the lead 40 when implanted within the coronary sinus. The primary and secondary spiraled portions 62, 64 may be used alone or in combination with one or more adhesions sites to provide the requisite positional stability of the lead 40 when implanted in the coronary sinus.

Figure 12:
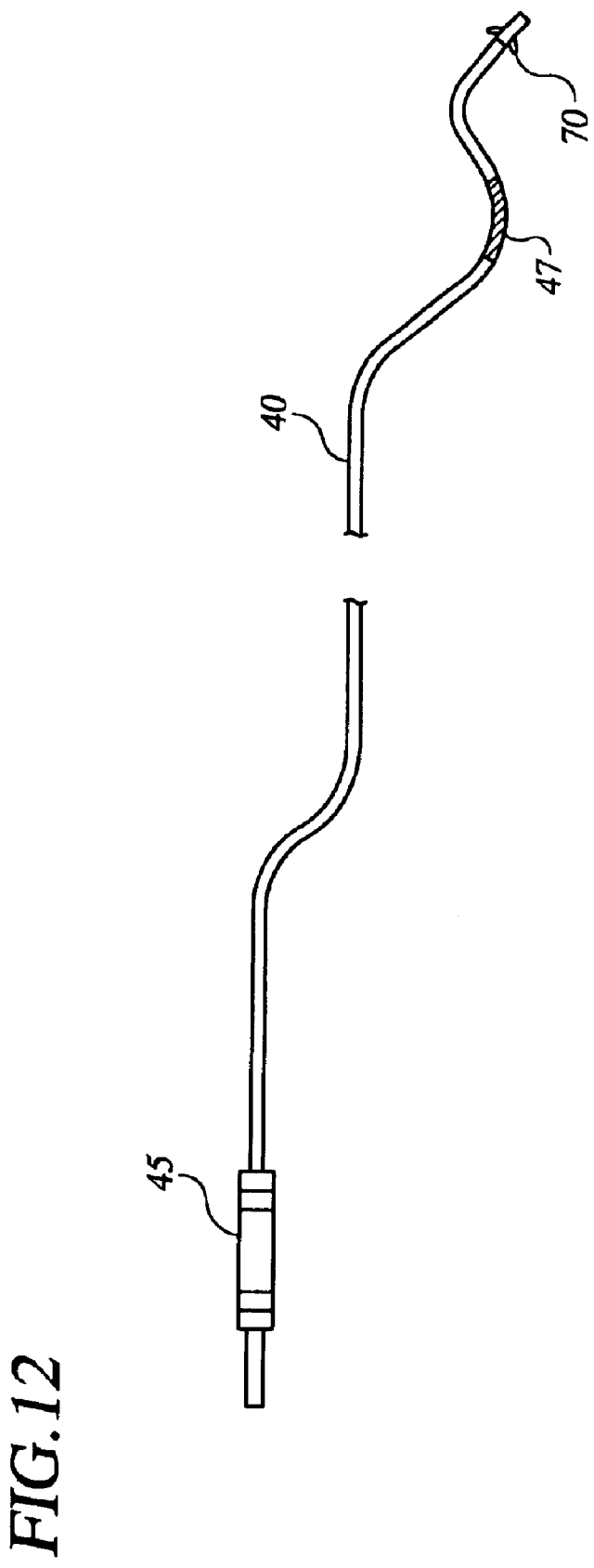
FIG. 12 illustrates a coronary sinus lead that incorporates tines in accordance with an embodiment of the present invention.

FIG. 12 illustrates a further embodiment of a coronary sinus lead system. In this embodiment, the lead 40 includes one or more tines 70 that can be situated at any location on the lead. In one configuration, tines 70 are situated toward the distal end of the lead 40. In addition to tines 70, the lead 40 depicted in FIG. 12 may include a primary spiraled portion, such as that shown in FIG. 11. One or more adhesion sites may be employed along with the tines 70, alone or in combination with a primary spiraled portion, to provide a desired level of positional lead stability.

It will, of course, be understood that various modifications and additions can be made to the preferred embodiments discussed hereinabove without departing from the scope of the present invention. For example, it will be appreciated by one skilled in the art that the lead fixation structures and methodologies of the present invention may be employed for leads and catheters requiring stabilization within body structures and vessels other than cardiac structures and vessels. Accordingly, the scope of the present invention should not be limited by the particular embodiments described above, but should be defined only by the claims set forth below and equivalents thereof.

What is claimed is:

1. An implantable cardiac lead system, comprising:
    a cardiac lead; and
    a sleeve arrangement provided on the lead, the sleeve arrangement comprising:
        one or more first locations comprising a first material that substantially prevents tissue in-growth between the first locations and cardiac tissue contacting the first locations; and
        one or more adhesion sites provided at the one or more first locations, the adhesion sites promoting tissue in-growth or attachment between the adhesion sites and cardiac tissue contacting the adhesion sites.

2. The system of claim 1, wherein the cardiac lead comprises one or more electrodes.

3. The system of claim 2, wherein the one or more electrodes comprise one or more of sensing, pacing, or shocking electrodes.

4. The system of claim 1, wherein the cardiac lead comprises one or more sensors.

5. The system of claim 4, wherein the one or more sensors comprise one or more of an accelerometer, pressure sensor, oxygen sensor, or temperature sensor.

6. The system of claim 1, wherein the lead system further comprises a drug delivery mechanism.

7. The system of claim 1, wherein the adhesion sites define apertures in the sleeve at the one or more first locations of the sleeve.

8. The system of claim 1, wherein the adhesion sites comprise a material that promotes cardiac tissue in-growth or attachment at the adhesion sites.

9. The system of claim 1, wherein the adhesion sites comprise exposed portions of the one or more electrodes.

10. The system of claim 1, wherein the adhesion sites comprise a structure having a porous surface that promotes cardiac tissue in-growth or attachment at the adhesion sites.

11. The system of claim 10, wherein the structure comprises a metallic annular structure.

12. The system of claim 1, wherein the first material comprises a first polymer material that substantially prevents tissue in-growth between the first locations and cardiac tissue contacting the first locations, and the adhesion sites comprise a second polymer material that promotes tissue in-growth or attachment between the adhesion sites and cardiac tissue contacting the adhesion sites.

13. The system of claim 12, wherein the second polymer material has a porosity differing from that of the first polymer material.

14. The system of claim 12, wherein the second polymer material has an average pore size differing from that of the first polymer material.

15. The system of claim 12, wherein the second polymer material has a distribution of pore sizes differing from that of the first polymer material.

16. The system of claim 12, wherein the second polymer material has a hydrophobicity differing from that of the first polymer material.

17. The system of claim 1, wherein the first material comprises a first type of PTFE, and a second material of the adhesion sites comprises a second type of PTFE.

18. The system of claim 1, wherein the first material comprises a first type of ePTFE, and a second material of the adhesion sites comprises a second type of ePTFE.

19. The system of claim 1, wherein the lead further comprises a bias mechanism proximate one or more of the adhesion sites.

20. The system of claim 19, wherein the bias mechanism comprises a biased coil electrode, a biased insulation material disposed on an outer layer of the lead, a biased structure operatively coupled to a lumen defined within the lead or a biased structure disposed on the outer layer of the lead.

21. An implantable cardiac lead system, comprising:
a lead comprising at least one electrode;
a sleeve covering all or a portion of the electrode;
a first fixation arrangement provided with the lead, the first fixation arrangement providing fixation between a first portion of the lead and coronary sinus vasculature or cardiac structure of the heart; and
a second fixation arrangement provided with the lead, the second fixation arrangement providing fixation between the coronary sinus vasculature or cardiac structure and a second portion of the lead, at least one of the first and second fixation arrangements comprising a spiraled portion of the lead.

22. The system of claim 21, wherein the first fixation arrangement comprises a first spiraled portion of the lead and the second fixation arrangement comprises a second spiraled portion of the lead.

23. The system of claim 22, wherein the second spiraled portion comprises silicone rubber or polyurethane rubber.

24. The system of claim 21, wherein:
the first fixation arrangement comprises a first spiraled portion of the lead, the first spiraled portion comprising at least a portion of the electrode; and
the second fixation arrangement comprises a second spiraled portion of the lead distal to the first spiraled portion.

25. The system of claim 21, wherein the first fixation arrangement or the second fixation arrangement comprises a tine.

26. An implantable cardiac lead system, comprising:
a lead comprising a electrode;
a first fixation arrangement comprising a spiraled portion of the lead that provides a first fixation mechanism between the lead and coronary sinus tissue; and
a second fixation arrangement that provides a second fixation mechanism between the lead and coronary sinus tissue, the second fixation arrangement comprising a polymer sleeve arrangement encompassing all or a portion of the electrode, the polymer sleeve arrangement comprising one or more adhesion sites for promoting coronary sinus tissue in-growth or attachment at the adhesion sites.

27. The system of claim 26, wherein the one or more adhesion sites of the polymer sleeve arrangement comprise a first material that promotes coronary sinus tissue in-growth or attachment at the adhesion sites.

28. The system of claim 26, wherein:
the polymer sleeve arrangement, other than at the one or more adhesion sites, comprises a first material that prevents coronary sinus tissue in-growth; and
the one or more adhesion sites comprise a second material that promotes coronary sinus tissue in-growth or attachment at the adhesion sites.

29. The system of claim 28, wherein the second material comprises a type of PTFE that promotes coronary sinus tissue in-growth or attachment.

30. The system of claim 28, wherein the second material comprises a type of ePTFE that promotes coronary sinus tissue in-growth or attachment.

31. The system of claim 28, wherein the first material comprises a type of PTFE or ePTFE that prevents coronary sinus tissue in-growth.

32. The system of claim 26, wherein the one or more adhesion sites of the polymer sleeve arrangement comprises one or more partial or complete gaps provided on the polymer sleeve arrangement.

33. The system of claim 32, wherein the gaps comprise between about 1 percent and about 10 percent of a surface area of the polymer sleeve arrangement.

34. The system of claim 32, wherein the gaps comprise a circumferential dimension and a longitudinal dimension, the circumferential dimension being greater than the longitudinal dimension.

35. The system of claim 32, wherein the gaps comprise a circumferential dimension and a longitudinal dimension, the circumferential dimension being less than the longitudinal dimension.

36. The system of claim 32, wherein the gaps comprise a circumferential dimension and a longitudinal dimension, the circumferential dimension being substantially equal to the longitudinal dimension.

37. The system of claim 26, wherein the spiraled portion of the lead comprises at least a portion of the electrode.

38. A method of stabilizing a lead passing into a coronary sinus of a heart, comprising:
providing a sleeve arrangement on the lead, the lead including one or more first locations comprising a first material and one or more adhesion sites provided at the one or more first locations;
substantially preventing tissue in-growth between the first locations and cardiac tissue contacting the first locations; and
promoting tissue in-growth or attachment between the adhesion sites and cardiac tissue contacting the adhesion sites to enhance stabilization of the lead passing into the coronary sinus.

39. The method of claim 38, further comprising producing electrical energy at one or more of the adhesion sites.

40. The method of claim 38, further comprising sensing electrical energy at one or more of the adhesion sites.

41. The method of claim 38, further comprising sensing one or more physiologic parameters at one or more of the adhesion sites.

42. The method of claim 38, wherein promoting tissue in-growth or attachment comprises promoting tissue in-growth or attachment via apertures defined at the adhesion sites.

43. The method of claim 38, wherein promoting tissue in-growth or attachment comprises promoting tissue in-growth or attachment using a material that promotes cardiac tissue in-growth or attachment at the adhesion sites.

44. The method of claim 38, wherein promoting tissue in-growth or attachment comprises promoting tissue in-growth or attachment using one or more exposed portions of the one or more electrodes.

45. The method of claim 38, wherein promoting tissue in-growth or attachment comprises promoting tissue in-growth or attachment using a porous surface structure having one or more of a porosity, pore sizes or distribution of pore sizes that promote cardiac tissue in-growth or attachment at the adhesion sites.

46. The method of claim 38, wherein the first material comprises a first polymer material that substantially prevents tissue in-growth between the first locations and cardiac tissue contacting the first locations, and promoting tissue in-growth or attachment comprises promoting tissue in-growth or attachment using a second polymer material at the adhesion sites that promotes tissue in-growth or attachment between the adhesion sites and cardiac tissue contacting the adhesion sites.

47. The method of claim 38, wherein a second material is disposed at the adhesions sites, the method further comprising varying one or more of a porosity, pore sizes or distribution of pore sizes of the second material to be different from that of the first polymer material.

48. The method of claim, 38, further comprising generating a bias force at or proximate one or more of the adhesion sites.

49. A method of stabilizing a lead passing into a coronary sinus of a heart, comprising:

providing a lead comprising at least one electrode;

stabilizing the lead at a first fixation location within a right atrium of the heart or a proximal portion of the coronary sinus; and stabilizing the lead at a second fixation location within a distal portion of the coronary sinus, a spiraled portion of the lead stabilizing the lead at at least one of the first and second fixation locations.

50. The method of claim 49, wherein:

stabilizing the lead at the first fixation location comprises mechanically stabilizing the lead at the first fixation location; and stabilizing the lead at the second fixation location comprises mechanically stabilizing the lead at the second fixation location.

51. The method of claim 50, wherein mechanically stabilizing the lead comprises using a first spiraled portion of the lead at the first fixation location and using a second spiraled portion of the lead at the second fixation location to stabilize the lead.

52. The method of claim 49, wherein:

stabilizing the lead at the first fixation location comprises mechanically stabilizing the lead at the first fixation location; and stabilizing the lead at the second fixation location comprises stabilizing the lead at the second fixation location using cellular adhesion at selected portions of coronary sinus vasculature.

53. The method of claim 49, wherein:

stabilizing the lead at the first fixation location comprises stabilizing the lead at the first fixation location using cellular adhesion at the first fixation location; and stabilizing the lead at the second fixation location comprises mechanically stabilizing the lead at the second fixation location.

54. The method of claim 49, further comprising delivering a drug using the lead.

55. An implantable cardiac lead system, comprising:

a lead comprising at least one electrode;

a sleeve covering all or a portion of the electrode;

a first fixation arrangement provided with the lead and comprising a spiraled portion of the lead, the first fixation arrangement providing fixation between a first portion of the lead and coronary sinus vasculature or cardiac structure of the heart; and a second fixation arrangement provided with the lead and comprising one or more adhesion sites provided with the sleeve for promoting tissue in-growth or attachment at the adhesion sites, the second fixation arrangement providing fixation between the coronary sinus vasculature or cardiac structure and a second portion of the lead.

56. The system of claim 55, wherein the adhesion sites define apertures in the sleeve.

57. The system of claim 55, wherein the adhesion sites comprise a material that promotes tissue in-growth or attachment at the adhesion sites.

58. The system of claim 55, wherein the adhesion sites comprise one or more exposed portions of the electrode.

59. The system of claim 55, wherein the adhesion sites comprise a porous surface structure having one or more of a porosity, pore sizes, or pore size distribution that promotes tissue in-growth or attachment at the adhesion sites.

* * * * *

UNITED STATES PATENT AND TRADEMARK OFFICE
CERTIFICATE OF CORRECTION

PATENT NO. : 6,961,621 B2
DATED : November 1, 2005
INVENTOR(S) : Krishnan et al.

It is certified that error appears in the above-identified patent and that said Letters Patent is hereby corrected as shown below:

Drawings,
Figure 1, "5VC" should read -- SVC --.

Column 4,
Line 17, "adhesions sites" should read -- adhesion sites --.

Column 5,
Line 49, "Illustrates" should read -- illustrates --.

Column 8,
Line 64, "lead 40 lead at" should read -- lead 40 at --.

Column 9,
Line 7, "proximal 2 – 5" should read -- proximal 2 – 4 --.
Line 57, "include on or" should read -- include one or --.

Column 11,
Line 14, "adhesions sites" should read -- adhesion sites --.
Line 15, "than a axial" should read -- than an axial --.
Line 22, "The adhesions" should read -- The adhesion --.
Line 62, "44c incorporated" should read -- 44a incorporated --.

Column 12,
Line 9, "more adhesions sites" should read -- more adhesion sites --.
Line 17, "FIG. 11" should read -- FIG 10 --.

Column 13,
Line 67, "comprising a electrode;" should read -- comprising an electrode; --.

UNITED STATES PATENT AND TRADEMARK OFFICE
CERTIFICATE OF CORRECTION

PATENT NO. : 6,961,621 B2
DATED : November 1, 2005
INVENTOR(S) : Krishnan et al.

It is certified that error appears in the above-identified patent and that said Letters Patent is hereby corrected as shown below:

Column 15,
Line 34, "adhesions sites" should read -- adhesion sites --.
Line 38, "claim, 38" should read -- claim 38 --.

Signed and Sealed this

Twenty-eighth Day of February, 2006

JON W. DUDAS
*Director of the United States Patent and Trademark Office*